United States Patent
Box et al.

(10) Patent No.: US 6,407,076 B1
(45) Date of Patent: Jun. 18, 2002

(54) ADENOSINE ANALOGUES AND RELATED METHOD OF TREATMENT

(75) Inventors: Philip Charles Box, Ware; Brian David Judkins, Baldock, both of (GB); Andrew Michael Kenneth Pennell, San Francisco, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/530,574

(22) PCT Filed: Nov. 6, 1998

(86) PCT No.: PCT/EP98/07022
  § 371 (c)(1),
  (2), (4) Date: Jun. 27, 2000

(87) PCT Pub. No.: WO99/24450
  PCT Pub. Date: May 20, 1999

(30) Foreign Application Priority Data

Nov. 8, 1997 (GB) .............................................. 9723566

(51) Int. Cl.$^7$ ........................ A61K 31/70; C07H 19/167
(52) U.S. Cl. .................. 514/46; 536/27.23; 536/27.62; 536/27.63
(58) Field of Search .............................. 514/46, 27.23; 536/27.62, 27.63

(56) References Cited

U.S. PATENT DOCUMENTS 5,561,134 A  * 10/1996 Spada et al. ................. 514/266
5,652,366 A  * 7/1997 Spada et al. ................. 546/118
5,736,554 A  * 4/1998 Spada et al. ................. 514/303
6,232,297 B1 * 5/2001 Linden et al. ................. 514/46

FOREIGN PATENT DOCUMENTS

| WO | WO 88/03147 A1 | * | 5/1988 |
| WO | WO 95 28160 A |   | 10/1995 |
| WO | WO 97 33591 A |   | 9/1997 |
| WO | WO 97 43300 A |   | 11/1997 |

OTHER PUBLICATIONS

Herdewijn et al., "Synthesis of Nucleosides Fluorinated in the Sugar Moiety. The Application of Diethylaminosulfur Trifluoride to the Synthesis of Fluorinated Nucleosides," *Nucleosides & Nucleotides*, 8(1), 65–96 (1989).*

Poulsen et al., "Adenosine Receptors: New Opportunities for Future Drugs," *Bioorganic & Medicinal Chemistry*, 6, 619–641 (1998).*

* cited by examiner

Primary Examiner—Gary Geist
Assistant Examiner—L. Eric Crane
(74) Attorney, Agent, or Firm—Bacon & Thomas

(57) ABSTRACT

A compound of formula (I) wherein $R^2$ represents $C_{1-3}$ alkyl, halogen or hydrogen; $R^3$ represents a fluorinated straight or branched alkyl group of 1–6 carbon atoms; and salts and solvates thereof, in particular, physiologically acceptable solvates and salts thereof. These compounds are agonists of the Adenosine A1 receptor.

26 Claims, No Drawings

ADENOSINE ANALOGUES AND RELATED METHOD OF TREATMENT

CHEMICAL COMPOUNDS

The present invention relates to novel adenosine derivatives, to processes for their preparation, to pharmaceutical compositions containing them and to their use in medicine. Adenosine derivatives and analogs which possess adenosine agonist activity that are useful as antihypertensive, cardioprotective, anti-ischemic and antilipolytic agents have been described in published International Application WO 95/28160.

The present invention provides compounds of formula (I) which are agonists at the adenosine A1 receptor

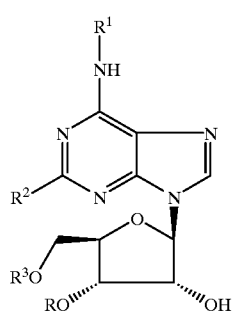

(I)

wherein $R^2$ represents $C_{1-3}$alkyl, halogen or hydrogen;
$R^3$ represents a fluorinated straight or branched alkyl group of 1–6 carbon atoms;
$R^1$ represents a group selected from
(1)—(alk)$_n$— ($C_{3-7}$) cycloalkyl, including bridged cycloalkyl, said cycloalkyl group being optionally substituted by one or more substituents selected from OH, halogen, —($C_{1-3}$) alkoxy, wherein (alk) represents $C_{1-3}$alkylene and n represents 0 or 1.
(2) an aliphatic heterocyclic group of 4 to 6 membered rings containing at least one heteroatom selected from O, N or S and optionally substituted by one or more substituents selected from the group consisting of —($C_{1-3}$)alkyl, —$CO_2$—($C_{1-4}$) alkyl, —$CO(C_{1-3}$alkyl), —$S(=O)_n$—($C_{1-3}$alkyl), —$CONR^aR^b$ (wherein $R^a$ and $R^b$ independently represent H or $C_{1-3}$alkyl), or =O; where there is a sulfur atom in the heterocyclic ring, said sulfur is optionally substituted by $(=O)_n$, where n is 1 or 2.
(3) Straight or branched $C_{1-12}$ alkyl, optionally including one or more O, $S(=O)_n$ (where n is 0, 1 or 2), or N groups substituted within the alkyl chain, said alkyl optionally substituted by one or more of the following groups; phenyl, halogen, hydroxy or $NR^aR^b$ wherein $R^a$ and $R^b$ both represent $C_{1-3}$alkyl or hydrogen.
(4) a fused bicyclic aromatic ring

wherein B represents a 5 or 6 membered heterocyclic aromatic group containing 1 or more O, N or S atoms wherein the bicyclic ring is attached to the nitrogen atom of formula (I) via a ring atom of ring A and ring B is optionally substituted —$CO_2$—($C_{1-3}$alkyl).

(5) a phenyl group optionally substituted by one or more substituents selected from:
—-halogen, —$SO_3H$, —(alk)$_n$OH, —(alk)$_n$-cyano, —(O)$_n$ —($C_{1-6}$) -alkyl (optionally substituted by one or more halogens), —(alk)$_n$—nitro, —(O)$_m$ —(alk)$_n$ —$CO_2R^c$, —(alk$_n$)—$CONR^cR^d$, —(alk)$_n$ —$COR^c$, —(alk)$_n$ —$SOR^e$, —(alk)$_n$ —$SO_2R^e$, —(alk)$_n$ —$SO_2NR^cR^d$, —(alk)$_n$—$OR^c$, —(alk)$_n$— (CO)$_m$—$NHSO_2R^e$, —(alk)$_n$ —$NHCOR^c$, —(alk)$_n$—$NR^cR^d$ wherein m and n are 0 or 1 and alk represents a $C_{1-6}$alkylene group or $C_{2-6}$ alkenyl group.
(6) A phenyl group substituted by a 5 or 6 membered heterocyclic aromatic group, said heterocyclic aromatic group optionally being substituted by $C_{1-3}$alkyl or $NR^cR^d$.
$R^c$ and $R^d$ may each independently represent hydrogen, or $C_{1-3}$ alkyl or when part of a group $NR^cR^d$, $R^c$ and $R^d$ together with the nitrogen atom may form a 5 or 6 membered heterocyclic ring optionally containing other heteroatoms, which heterocyclic ring may optionally be substituted further by one or more $C_{1-3}$ alkyl groups.
$R^e$ represents $C_{1-3}$alkyl.

and salts and solvates thereof, in particular, physiologically acceptable solvates and salts thereof.

Conveniently, the adenosine A1 agonists of the general formula (I) above exhibit greater activity at the adenosine A1 receptor than the other adenosine receptor subtypes, particularly A3.

More particularly the compounds exhibit little or no activity at the A3 receptor.

It will be appreciated that wherein $R^1$ and/or $R^2$ in compounds of formula (I) contain one or more asymmetric carbon atoms the invention includes all diastereoisomers of compounds of formula (I) and mixtures thereof. Otherwise the stereochemical configuration of compounds of the invention is as depicted in formula (I) above.

As used herein, the term "alkyl" means a straight or branched alkyl group. Examples of suitable alkyl groups within $R^1$ and $R^2$ include methyl, ethyl, n-propyl, i-propyl, n-butyl, s-butyl, t-butyl and 2,2-dimethylpropyl.

As used herein, the term "alkylene" means a straight or branched chain alkylene group containing 1 to 6 carbon atoms e.g. methylene.

As used herein, the term "$C_{2-6}$alkenyl" means a straight or branched chain alkenyl group containing 2 to 6 carbon atoms. Allyl represents an example of a suitable $C_{2-6}$alkenyl group.

The term "halogen" means fluorine, chlorine, bromine or iodine.

By aliphatic heterocyclic group is meant a cyclic group of 4–6 carbon atoms wherein one or more of the carbon atoms is/are replaced by heteroatoms independently selected from nitrogen, oxygen or sulfur. This group may optionally be substituted as defined hereinabove.

The term heterocyclic aromatic group refers to an aromatic mono or bicyclic ring system comprising from 5 to 10 carbon atoms wherein one or more of the carbon atoms is/are replaced by heteroatoms independently selected from nitrogen, oxygen and sulfur, which ring system may optionally be substituted as defined hereinabove.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulfonic, formic, benzoic, malonic, naphthalene-2-sulfonic and benzenesulfonic acids. A particularly suitable pharmaceutically acceptable salt of the compounds of formula (I) is the hydrochloride salt. Other acids such as oxalic, while not in themselves pharmaceutically acceptable, may be useful as intermediates in obtaining the compounds of the invention and their pharmaceutically acceptable acid addition salts. The solvates may be, for example, hydrates.

$R^3$ preferably represents a $C_{1-3}$ fluoroalkyl group especially a fluoromethyl group. More preferably $R^3$ represents a trifluromethyl group.

$R^2$ preferably represents hydrogen, methyl or halogen, more preferably hydrogen, methyl or chlorine.

Conveniently, $R^1$ may represent (alk)$_n$—$C_{3-6}$-cycloalkyl wherein n is 0 or 1 and the said cycloalkyl is either substituted by at least one substituent selected from halogen, particularly fluorine, and OH or is unsubstituted. Preferably, n represents zero. More preferably, the cycloalkyl group is monosubstituted by OH or fluorine. More preferably the cycloalkyl ring has 5 carbon members.

Alternatively $R^1$ may represent a substituted or unsubstituted aliphatic heterocyclic group, the substituent being selected from the group consisting of —(CO$_2$)—(C$_{1-4}$)alkyl —CO—(C$_{1-3}$)alkyl, —S(=O)$_n$—(C$_{1-3}$)alkyl, CONR$^a$R$^b$ wherein R$^a$ and R$^b$ are defined herein above, and when there is a heteroatom S in the ring, this heteroatom may optionally be substituted by (=O), where n is 0, 1 or 2. More preferably the heterocyclic ring is unsubstituted or the substituents are —CO$_2$(C$_{1-4}$)alkyl, or when the heteroatom is S, the substituent (=O)$_n$ is attached to the heterocyclic S atom. More preferably, when there is a sulfur heteroatom in the ring this S is unsubstituted.

Conveniently the alphatic heterocyclic group is unsubstituted or when the substituent is —CO$_2$(C$_{1-4}$)alkyl the heteroatom is nitrogen and the substituent is attached directly to said ring nitrogen atom.

Preferably the heterocyclic ring is 5 or 6 membered and more preferably contains only one O, N or S heteroatom.

Alternatively, $R^1$ may represent a straight or branched alkyl of 1–5 carbon atoms optionally with at least one S (=O)$_n$ where n=0, 1 or 2 and/or N—H substituted in the chain. Where there is an S(=O)$_n$ in the chain, preferably n is 1 or 2. The alkyl group conveniently may be unsubstituted or substituted by at least one OH group.

Alternatively $R^1$ may represent a phenyl group which is substituted by one or more substituents selected from OH and halogen. Preferably the phenyl is disubstituted in the 2,4 positions. Preferably both substituents are halogen more particularly, fluorine and chlorine. For example, a particularly preferred combination is 2-fluoro and 4-chloro.

It is to be understood that the present invention covers all combinations of particular and preferred groups mentioned above.

Particular compounds according to the invention include:

N-(Tetrahydro-pyran-4-yl)-5'-O-trifluoromethyl-adenosine,

N-(2-Pyridin-4-yl-ethyl)-5'-O-trifluoromethyl-adenosine,

N-(2S-Fluoro-cyclopent-(S)-yl)-5'-O-trifluoromethyl-adenosine,

N-(Tetrahydro-thiopyran-4-yl)-5'-O-trifluoromethyl-adenosine,

N-(3,4-Difluoro-phenyl)-5'-O-trifluoromethyl-adenosine,

N-(3-Fluoro-phenyl)-5'-O-trifluoromethyl-adenosine,

N-(exo-Bicyclo[2.2.1]hept-2-yl)-5'-O-trifluoromethyl-adenosine,

N-(1,1-Dioxo-hexahydro-1.delta.6-thiopyran-4-yl)-5'-O-trifluoromethyl-adenosine, N-tert-Butyl-5'-O-trifluoromethyl-adenosine, 4-[9-(3R,4S-Dihydroxy-5R-trifluoromethoxymethyl-tetrahydro-furan-2R-yl)-9H-purin-6-ylamino]-piperidine-1-carboxylic acid ethyl ester, N-(2S-Hydroxy-cyclopent-(S)-yl)-5'-O-trifluoromethyl-adenosine, N-(rel-2,3-Dihydroxy-propyl)-5'-O-trifluoromethyl-adenosine, N-(Tetrahydro-furan-3R-yl)-5'-O-trifluoromethyl-adenosine, N-(Tetrahydro-furan-3S-yl)-5'-O-trifluoromethyl-adenosine, N-{2-[9-(3R,4S-Dihydroxy-5R-trifluoromethoxymethyl-tetrahydro-furan-2R-yl)-9H-purin-6-ylamino]-ethyl}-acetamide, 5'-O-Trifluoromethyl-adenosine, 2-[9-(3R,4S-Dihydroxy-5R-trifluoromethoxymethyl-tetrahydro-furan-2R-yl)-9H-purin-6-ylamino]-ethanesulfonic acid methylamide, 4-[9-(3R,4S-Dihydroxy-5R-trifluoromethoxymethyl-tetrahydro-furan-2R-yl)-2-methyl-9H-purin-6-ylaminol-piperidine-1-carboxylic acid ethyl ester, 2-methyl N-(tetrahydro-pyran-4-yl)-5'-O-trifluoromethyl-adenosine, 5'-O-(3-Fluoro-propyl)-N-(tetrahydro-pyran-4-yl)-adenosine, 2-Chloro-5'-O-(3-fluoro-propyl)-N-(tetrahydro-pyran-4-yl)-adenosine, N-Cyclopentyl-5'-O-(2,2,2-trifluoro-ethyl)-adenosine, N-(Tetrahydro-pyran-4-yl)-5'-O-(2,2,2-trifluoro-ethyl)-adenosine, N-(2R-Hydroxy-cyclopent-(R)-yl)-5'-O-(2,2,2-trifluoro-ethyl)-adenosine, N-(4-Fluoro-phenyl)-5'-O-(2,2,2-trifluoro-ethyl)-adenosine.

Compounds according to the invention have applicability as inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose, insulin and ketone body levels and therefore may be of value in the therapy of diabetes. Since anti-lipolytic agents have hypolipidaemic and hypofibrinogenaemic activity, the compounds may also show anti-atherosclerotic activity. The anti-lipolytic activity of compounds of the invention has been demonstrated by their ability to lower the concentration of non-esterified fatty acids (NEFA) in starved rats dosed orally according to the method described by P. Strong et al. in Clinical Science (1993), 84, 663–669.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina.

Furthermore, the compounds of the invention are useful as cardioprotective agents, having applicability in the treatment of ischaemic heart disease. As used herein the term "ischaemic heart disease" includes damage associated with both myocardial ischaemia and reperfusion, for example, associated with coronary artery bypass grafting (CABG), percutaneous translumenal coronary angioplasty (PTCA), cardioplegia, acute myocardial infarction, thrombolysis, stable and unstable angina and cardiac surgery including in particular cardiac transplantation. The compounds of the invention additionally are useful for treating ischaemic damage to other organs. The compounds of the invention may also be valuable in the treatment of other disorders arising as a result of widespread atheromatous disease, for example, peripheral vascular disease (PVD) and stroke.

The compounds may also inhibit renin release and thus be of use in the therapy of hypertension and heart failure. The compounds may also be useful as CNS agents (e.g. as hypnotics, sedatives, analgestics and/or anti-convulsants particularly finding use in the treatment of epilepsy).

In addition, the compounds of the invention may find use in the treatment of sleep apnoea.

The compound of formula (I) and pharmaceutically acceptable acid addition salts thereof are useful as analgesics. They are therefore useful in treating or preventing pain. They may be used to improve the condition of a host, typically of a human being, suffering from pain. They may be employed to alleviate pain in a host. Thus, the compound of formula (I) and its pharmaceutically acceptable acid addition salts may be used as a preemptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, diabetic neuropathies associated with diabeties, trigeminal neuralgia, pain associated with functional bowel disorders, e.g. irritable bowel syndrome, non cardiac chest pain and sympathetically maintained pain) and pain associated with cancer and fibromyalgia. The compound of formula (I) may also be used in the treatment or prevention of pain associated with migraine, tension headache and cluster headaches, pain associated with functional bowel disorders (e.g. IBS), non cardiac chest pain and non ulcer dyspepsia.

Accordingly, the invention provides a compound of formula (I) or a physiologically acceptable salt or solvate thereof for use in therapy, and in particular in the treatment of human or animal subjects suffering from a condition in which there is an advantage in decreasing plasma free fatty acid concentration, or reducing heart rate and conduction, or whereby the therapy involves the treatment of ischaemic heart disease, peripheral vascular disease or stroke or which subject is suffering from a CNS disorder, steep apnoea or pain.

In a further aspect, the invention provides a method of treatment of a human or animal subject suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering a CNS disorder or suffering from sleep apnoea or suffering pain, which method comprises administering to the subject an effective amount of a compound of formula (I) or a pharmaceutically acceptable salt or solvate thereof.

In respect of the above mentioned ischaemic treatment, it has been found that according to a particularly unexpected aspect of the present invention, not only does administration of a compound of formula (I) prior to ischaemia provide protection against myocardial infarction, but protection is also afforded if the compound of formula (I) is administered after the ischaemic event and before reperfusion. This means that the methods of the present invention are applicable not only where ischaemia is planned or expected, for example in cardiac surgery, but also in cases of sudden or unexpected ischaemia, for example in heart attack and unstable angina.

It will be appreciated that reference to treatment includes acute treatment or prophylaxis as well as the alleviation of established symptoms.

In yet a further aspect, the invention provides a pharmaceutical composition comprising at least one compound of formula (I) or a pharmaceutically acceptable salt or solvate thereof in association with a pharmaceutical carrier and/or excipient.

In another aspect, the invention provides a pharmaceutical composition comprising, as active ingredient, at least one compound of formula (I) or a pharmaceutically acceptable salt or solvate thereof in association with a pharmaceutical carrier and/or excipient for use in therapy, and in particular in the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering from a CNS disorder, sleep apnoea or pain.

There is further provided by the present invention a process of preparing a pharmaceutical composition, which process comprises mixing at least one compound of formula (I) or a pharmaceutically acceptable salt or solvate thereof, together with a pharmaceutically acceptable carrier and/or excipient.

Compositions according to the invention may be formulated for topical, oral, buccal, parenteral or rectal administration or in a form suitable for administration by inhalation or insufflation. Oral administration is preferred. The compositions may be adapted for sustained release.

For topical administration, the pharmaceutical composition may be given in the form of a transdermal patch.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 1 mg to 2 g, preferably 1 mg to 100 mg, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a pharmaceutically acceptable salt or solvate thereof for the manufacture of a medicament for the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease (PVD) or stroke, or which patient is suffering from a CNS disorder, sleep apnoea or pain.

The compounds of formula (I) and physiologically acceptable salts or solvates thereof may be prepared by the processes described hereinafter, said processes constituting a further aspect of the invention. In the following description, the groups $R^1$, $R^2$ and $R^3$ are as defined for compounds of formula (I) unless otherwise stated.

According to a first general process (A), a compound of formula (I) may be prepared by reacting a compound of formula (II).

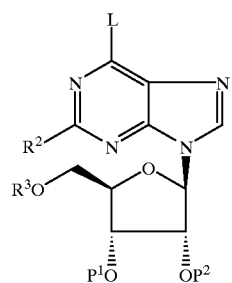

(II)

wherein, L represents a leaving group such as a halogen atom (e.g. a chlorine atom) and $P^1$ and $P^2$ represent hydrogen or a suitable protecting group (e.g. acetyl) with a compound of formula $R^1NH_2$ or a salt thereof, under basic conditions.

Compounds of formula (II) may be used to produce compounds of formula (I) directly by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine.

This reaction may be preceded or followed where appropriate by in situ removal of the $P^1$ and $P^2$ protecting groups.

For example when $P^1$ and $P^2$ represent acetyl, this may be effected with an amine such as ammonia or tert butylamine in a solvent such as methanol at a convenient temperature.

Compounds of formula (II) may be prepared by the reaction of a compound of formula (III).

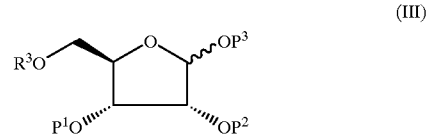

(III)

wherein $P^3$ represents a suitable protecting group for example $C_{1-3}$alkyl or acetyl, and $P^1$, $P^2$ and $R^3$ are as defined above, with a compound of formula (IV)

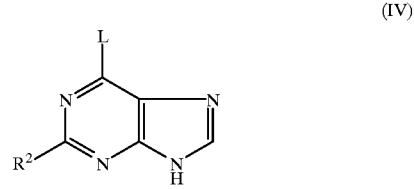

(IV)

wherein L and $R^2$ are as defined above.

The reaction is conveniently carried out in a suitable solvent, such as acetonitrile in the presence of a silylating agent such as trimethylsilyl trifluoromethane sulfonate and a base such as diazabicyclo [5.4.0]undec-7-ene (DBU). Alternatively the compound of formula (IV) may first be silylated with a suitable silylating agent, for example, hexamethyldisilazane reaction of the silylated intermediate with a compound of formula (III) and followed by a suitable Lewis acid, e.g. trimethylsilyl trifluoromethanesulfonate in a suitable solvent such as acetonitrile.

Compounds of formula (IV) are either known in the art or may be prepared from known compounds using methods analogous to those used to prepare the known compounds of formula (IV).

Compounds of formula (III) may be prepared from alternative protected compounds by replacement of the alternate protecting groups with $P^1$ and $P^2$; for example when $P^1$ and $P^2$ represent acetyl, compounds of formula (III) may be prepared from compounds of formula (V) wherein $P^4$ and $P^5$ represent $C_{1-3}$ alkyl and P3 is as defined above, by acid catalysed removal of the alkylidine protecting group, e.g. with hydrogen chloride in methanol, followed by in situ acylation for example with acetic anhydride in the presence of a base such as pyridine, in a solvent such as dichloromethane.

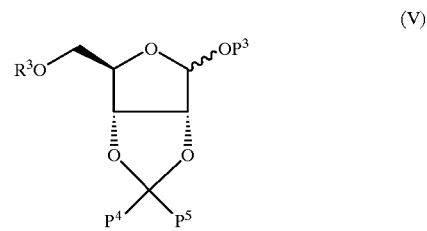

(V)

Compounds of formula (V) are known compounds or prepared by methods analagous to those used in the art to prepare the known compounds of formula (V). For example compounds of formula (V) wherein $P^3$, $P^4$ and $P^5$ represent methyl and $R^3$ represents $CF_3$ may be prepared from the known compound (VI) shown below

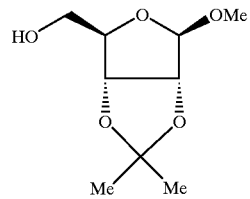

(VI)

by reacting (VI) with a suitable base, e.g. sodium hydride followed by carbon disulphide together with an alkylating agent $R^4L$ where L is a leaving group such as halogen (e.g. a bromine or iodine atom) and $R^4$ is an alkyl group as previously defined, for example, methyl iodide to produce the compound (VII).

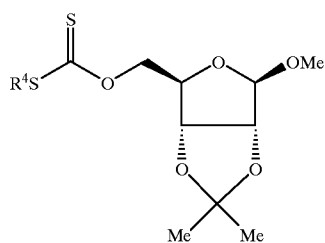

(VII)

Compound (VII) maybe treated with a suitable brominating agent, e.g. dibromomethylhydrantoin, and a pyridineihydrogen fluoride complex in a suitable solvent such as dichloromethane according to the method of Hiyoma T. et. al., Tetrahedron Letters 1992, 4173–4176 to produce the compound of formula (V).

Alternatively the known compound (VIII) shown below can be reacted with tris(dimethylamino) sulfur trifluoromethoxide in a suitable solvent such as dichloromethane

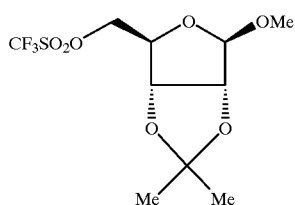

(VIII)

to produce the compound of formula (V).

It will be appreciated by a skilled person that the acetyl group in any of the compounds above could be replaced with any suitable protecting group, for example, other esters.

By analogous methods, compounds of formula (I) or (II) may also be prepared from compounds wherein alkylidene groups defined by $P^4$ and $P^5$ replace $P^1$ and $P^2$. This reaction represents an exchange of one protecting group for another and such reactions will be apparent to a person skilled in the art.

A further process (B) comprises converting a compound of formula (I) into a different compound of formula (I) by modifying the $R^1$, $R^2$ or $R^3$ group therein.

Compounds of formula (II) may also conveniently be prepared by the removal of the alkylidene protecting group from a compound of formula (IX)

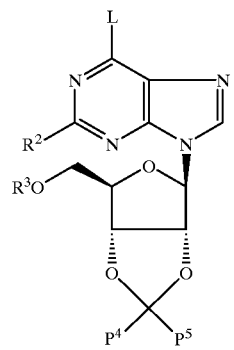

(IX)

wherein $P^4$, $P^5$ $R^3$, $R^2$ and L are as defined previously under the conditions described hereinabove.

Compounds of formula (IX) may be prepared by treating a compound of formula (X)

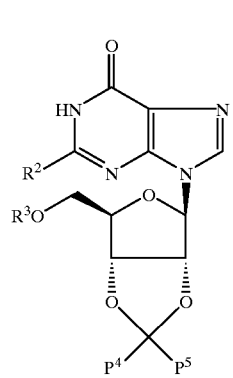

(X)

wherein $P^4$ and $P^5$ are as defined previously with a halogenating (e.g. chlorinating) agent under conventional conditions. Thus, for example, chlorination may conveniently be effected by treating (X) with phosphorus oxychloride in the presence of an organic base such as 4-dimethylaminopyridine and in a suitable solvent such as acetonitrile at an elevated temperature (e.g. up to the reflux temperature of the solvent).

Compounds of formula (X) may be prepared from compounds of formula (XI)

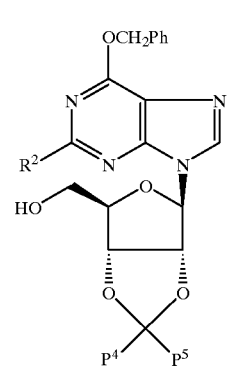

(XI)

by reaction with hydrogen or a source of hydrogen such as ammonium formate in the presence of a suitable catalyst such as palladium or carbon in a suitable solvent such as ethanol.

Compounds of formula (XI) may be prepared from compounds of formula (XII).

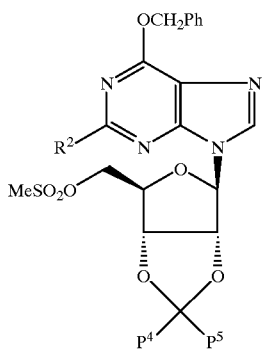

(XII)

by reaction with an alcohol $R^3OH$ in the presence of a strong base such as sodium hydride in a suitable inert solvent such as dimethylformamide.

Compounds of formula (XII) may be prepared from compounds of formula (XIII)

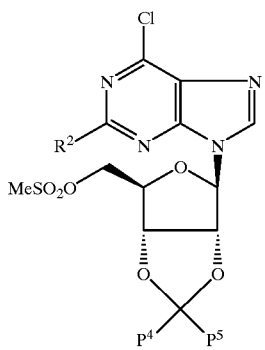

(XIII)

by reacting with benzyl alcohol in the presence of a suitable strong base such as sodium hydride in an inert solvent such as tetrahydrofuran.

Compounds of formula (XIII) may be prepared from compounds of formula (XIV) by reaction with methane sulfonyl chloride in the presence of a suitable base such as triethylamine, diisopropylethylamine or pyridine in a suitable solvent such as dichloromethane.

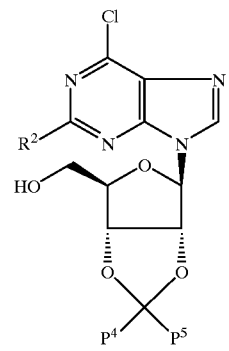

(XIV)

It will be appreciated that $R^1$ or $R^2$ or $R^3$ may be converted into a different $R^1$, or $R^2$ or $R^3$ grouping as an intermediate step in the overall synthesis of compounds of the invention whereas process (B) hereinabove merely describes interconversion as a final step process.

Compounds of formula (XIV) are either known in the art or may be prepared from known compounds using methods analogous to those used in the art to prepare the known compounds of formula (XIV).

Certain compounds of formulae (II), (III) and (V) are novel intermediates and form a further aspect of the present invention.

Compounds of the formula $R^1NH_2$ are either known compounds or may be prepared from known compounds using conventional procedures with some exceptions indicated in the experimental section hereinbelow.

In an alternative process (C) compounds of formula (I) may be prepared from compounds of formula (XV).

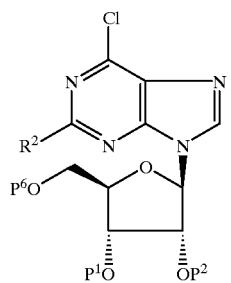

(XV)

wherein $P^1$ and $P^2$ are suitable protecting groups as defined above and $P^6$ also represents a suitable protecting group. For example when $R^2$ represents Cl, conveniently $P^1$, $P^2$ and $P^6$ all represent benzoyl (this is a known compound).

Compounds of formula (XV) may be used to produce compounds of formula (I) by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine.

This reaction may be preceded or followed where appropriate by in situ removal of the $P^1$, $P^2$ and $P^6$ protecting groups. For example when $P^1$, $P^2$ and $P^6$ represent benzoyl, this may be effected with a carbonate such as potassium carbonate in a solvent such as methanol to form a compound of formula (XVI).

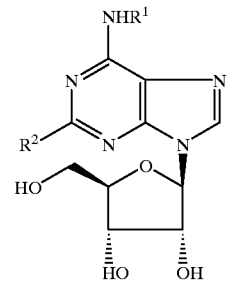

(XVI)

By reacting a compound of (XVI) with protecting groups P⁴ and P⁵ as defined above a compound of formula (XVII) may be formed.

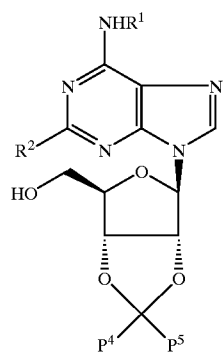

(XVII)

The R³ group may then be introduced into the compound in methods apparent to those skilled in the art followed by deprotection of the compound as described in Process A above.

Specific optical isomers of a compound of formula (I) may be obtained by conventional methods for example, by synthesis from an appropriate asymmetric starting material using any of the processes described herein, or where appropriate by separation of a mixture of isomers of a compound of formula (I) by conventional means e.g by fractional crystallisation or chromatography.

In the general processes described above, the compound of formula (I) obtained may be in the form of a salt, conveniently into the form of a pharmaceutically acceptable salt. Where desired, such salts may be converted into the corresponding free bases using conventional methods.

Pharmaceutically acceptable acid addition salts of the compounds of formula (I) may be prepared by reacting a compound of formula (I) with an appropriate acid in the presence of a suitable solvent such as acetonitrile, acetone, chloroform, ethyl acetate or an alcohol (e.g. methanol, ethanol or isopropanol). Pharmaceutically acceptable base addition salts may be obtained in an analogous manner by treating a solution of a compound of formula (I) with a suitable base. Pharmaceutically acceptable salts may also be prepared from other salts, including other pharmaceutically acceptable salts of the compounds of formula (I), using conventional methods.

The invention is further illustrated by the following non-limiting Intermediates and Examples.

Standard HPLC conditions are as follows:

Standard Automated Preparative HPLC Column, Conditions & Eluent

Automated preparative high performance liquid chromatography (autoprep. HPLC) was carried out using a Supelco® ABZ+ 5 μm 100 mm×22 mm i.d. column eluted with a mixture of solvents consisting of i) 0.1% formic acid in water and ii) 0.05% formic acid in acetonitrile, the eluant being expressed as the percentage of ii) in the solvent mixture, at a flow rate of 4 ml per minute. Unless otherwise stated the eluent was used as a gradient of 0–95% (ii) over 20 minutes.

LC/MS System

This system used an ABZ+PLUS, 3.3cm×4.6 mm i.d. column, eluting with solvents: A—0.1% v/v formic acid+ 0.077% w/v ammonium acetate in water; and B—95:5 acetonitrile:water+0.05% v/v formic acid, at a flow rate of 1 ml per minute. The following gradient protocol was used: 100% A for 0.7 mins; A+B mixtures, gradient profile 0–100% B over 3.5 mins; hold at 100% B for 3.5 mins; return to 100% A over 0.3 mins. The system used a micromass 'platform' spectrometer, with electrospray ionisation mode, positive and negative ion switching, mass range 80–1000 a.m.u.

HPLC System

The analytical HPLC system used an Inertsil® ODS2 150 mm×4.6 mm i.d. column, eluting with solvents: A—0.1% v/v phosphoric acid in water and B—95:5 acetonitrile:water+0.1% v/v phosphoric acid. The following gradient protocol was used with a flow rate of 1.0 mL/min: 100% A for 2 min; A+B mixtures, gradient profile 0–100% B over 40 min; hold at 100% B for 10 min.

Flash chromatography was carried out over Merck silica gel® (Merck 9385), or Merck alumina® (Merck 1077).

INTERMEDIATE 1

Dithiocarbonic Acid O-(6R-Methoxy-2,2-dimethyl-tetrahydro-(3aR,6aR)-furo[3,4]-d][1,3]dioxol-4R-ylmethyl) Ester S-methyl Ester

[6R-methoxy-2,2-dimethyl-tetrahydro-(3aR,6aR)-furo-[3,4-d][1,3]dioxol-4R-yl]-methanol (5.20 g) was dissolved in dry THF (70 ml) and treated portionwise over 10 min with 60% sodium hydride in oil (1.20 g) under nitrogen at 22° C. After 20 min, carbon disulphide (5 ml, 6.33 g) was added, and the mixture stirred for a further 20 min at 22° C. Iodomethane (2 ml) was added and after a further 0.5 h at 22° C., the solvent was removed in vacuo and the residue treated with water (80 ml) and extracted with ethyl acetate. The combined ethyl acetate extracts were dried (Na₂SO₄) and evaporated in vacuo to afford the product as a pale yellow oil (8.60 g).

TLC SiO₂ (cyclohexane-ether 1:1) Rf=0.62.

INTERMEDIATE 2

(3aR,4R,6R,6aR)-4-Methoxy-2,2-dimethyl-6-trifluoromethoxymethyl-tetrahydro-furo[3,4-d][1,3]dioxole 1,3-Dibromo-5,5-dimethylhydantoin (4.29 g) was suspended in dichloromethane (20 ml) and hydrogen fluoride-pyridine complex (10 ml, ca 80 eq.) added. The mixture was cooled to −70° C. under nitrogen and a solution of dithiocarbonic acid O-(6R-methoxy-2,2-dimethyl-tetrahydro-(3aR,6aR)-furo[3,4-d][1,3]dioxol-4R-ylmethyl) ester S-methyl ester (1.472 g) in dichloromethane (10 ml) added. The mixture was then stirred at 0–5° C. for 1 h before being quenched by slow addition to a mixture of 2M sodium carbonate (250 ml) containing sodium metabisulphite (10 g). Dichloromethane (60 ml) was added and the aqueous layer further extracted with dichloromethane (100 ml). The combined dichloromethane extracts were washed with 5% sodium metabisulphite solution, 2M sodium carbonate solution, dried (Na₂SO₄) and evaporated in vacuo. The residue was purified by flash chromatography over silica (150 g) eluting with cyclohexane-ether (4:1–2:1) to give the title compound as a clear oil (650 mg). TLC SiO₂ (cyclohexane-ether 1:1) Rf=0.5.

INTERMEDIATE 2 (alternative route)

Trifluoro-methanesulfonic acid 6R-methoxy-2,2-dimethyl-tetrahydro-(3aR,6aR)-furo[3,4-d][1,3]dioxol-4R- ylmethyl ester (1 g) was dissolved in dichloromethane (20 ml) and treated with tris(dimethylamino)sulfonium trifluoromethoxide (1.12 g), and stirred at 22° C. for 16 h under nitrogen. The solution was evaporated in vacuo and the residue purified by flash chromatography over silica (25 g) eluting with cyclohexane-ether (4:1) to afford the title compound as a clear oil (237 mg).

INTERMEDIATE 3

Acetic Acid 2R,4R-diacetoxy-5R-trifluoromethoxymethyl-tetrahydro-furan-3R-yl Ester (α Anomer) and Acetic Acid 2S,4R-diacetoxy-5R-trifluoromethoxymethyl-tetrahydro-furan-3R-yl Ester (β Anomer)

(3aR,4R,6R,6aR)4-Methoxy-2,2-dimethyl-6-trifluoromethoxymethyl-tetrahydro-furo[3,4-d][1,3]dioxole (0.61 g) was dissolved in a 9:1 mixture of trifluoroacetic acid-water (10 ml) and allowed to stand for 1 h at 22°. The solvent was removed in vacuo and the residue co-evaporated with toluene. The residue was dissolved in dichloromethane (15 ml)-pyridine (5 ml) and 4-dimethylaminopyridine (5 mg) and acetic anhydride (3 ml) added and the solution allowed to stand at 22° C. for 17 h. The mixture was concentrated in vacuo and the residue dissolved in ethyl acetate (150 ml), washed with 2M hydrochloric acid, and 8% sodium bicarbonate, dried ($Na_2SO_4$) and evaporated in vacuo. Flash chromatography over silica (30 g) eluting with cyclohexane-ether (3:1–1:1) gave firstly acetic acid 2S,4R-diacetoxy-5R-trifluoromethoxymethyl-tetrahydro-furan-3R-yl ester (β anomer) (237 mg), followed by acetic acid 2R,4R-diacetoxy-5R-trifluoromethoxymethyl-tetrahydro-furan-3R-yl ester (α anomer) (202 mg).

(β anomer) mass spectrum m/z 362 ($MNH_4^+$); (α anomer) mass spectrum m/z 362 ($MNH_4^+$).

INTERMEDIATE 4

Acetic Acid 4R-Acetoxy-5R-methoxy-2R-trifluoromethoxymethyl-tetrahydro-furan-3R-yl Ester (3aR,4R,6R,6aR)-4-Methoxy-2,2-dimethyl-6-trifluoromethoxymethyl-tetrahydro-furo[3,4-d][1,3]dioxole (6.67 g) was dissolved in methanol (100 ml) and treated with conc. hydrochloric acid (3.0 ml) and heated under reflux for 65 h. After 24 and 48 h, 20 ml methanol was distilled off and fresh methanol (20 ml) added to the reaction mixture. The solution was evaporated in vacuo and the residue co-evaporated with pyridine (10 ml), and the residue dissolved in dichloromethane (150 ml)-pyridine (15 ml). 4-Dimethylaminopyridine (ca. 20 mg) and acetic anhydride (9 ml) were added and the solution allowed to stand for 24 h at 22° C. The solvents were removed in vacuo and the residue treated with 8% sodium bicarbonate (150 ml), and extracted with ethyl acetate (2×150 ml). The organic extracts were dried ($Na_2SO_4$) and evaporated in vacuo and the residue purified by flash chromatography over silica (300 g) eluting with cyclohexane-ether (2:1–1:1) to give the title compound (2.45 g) as a colourless oil.

TLC $SiO_2$ (ether) Rf=0.72.

INTERMEDIATE 5

Acetic Acid 4R-Acetoxy-2R-(6-chloro-purin-9-yl)-5R-trifluoromethoxymethyl-tetrahydro-furan-3R-yl Ester 6-Chloropurine (0.770 g), 1,1,1,3,3,3-hexamethyldisilazane (4 ml, 18.96 mmol) and toluene (10 ml) were heated under reflux under nitrogen for 3 h. The solvent was removed in vacuo and the residue co-evaporated with toluene (10 ml). The residue was taken into dry acetonitrile (12 ml) and treated with acetic acid 2S,4R-diacetoxy-5R-trifluoromethoxymethyl-tetrahydro-furan-3R-yl ester (425 mg), 1,8-diazabicycloundec-7-ene (0.28 ml) and trimethylsilyl trifluoromethanesulfonate (0.41 ml) and stirred at 22° C. for 20 h under nitrogen, then heated under reflux for 2 h. The resulting orange solution was cooled to 20°, poured into 8% sodium bicarbonate solution (100 ml) and extracted with ethyl acetate. The organic extracts were dried ($Na_2SO_4$) and evaporated in vacuo and the residue purified by flash chromatography over silica (60 g) eluting with cyclohexane-ether (1:1–1:4 gradient) to afford the title compound (345 mg).

TLC $SiO_2$ ($Et_2O$) Rf=0.6.

INTERMEDIATE 5 (alternative route)

6-Chloropurine (0.31 g), 1,1,1,3,3,3-hexamethyldisilazane (2 ml) and toluene (6 ml) were heated under reflux under nitrogen for 2 h. The solvent was removed in vacuo and the residue co-evaporated with dry toluene. The solid residue was dissolved in dry acetonitrile (12 ml) and acetic acid 4R-acetoxy-5R-methoxy-2R-trifluoromethoxymethyl-tetrahydro-furan-3R-yl ester (0.29 g), 1,8-diazabicycloundec-7-ene (0.24 ml), and trimethylsilyl trifluoromethanesulfonate (0.35 ml) added and the solution heated under reflux under nitrogen for 2 h, cooled, and allowed to stand for 17 h at 22° C. Further trimethylsilyl trifluoromethanesulfonate (0.35 ml) was added, and the solution heated under reflux under nitrogen for a further 5 h. The solution was added to 8% sodium bicarbonate (30 ml) and extracted with dichloromethane. The organic extracts were dried ($Na_2SO_4$) and evaporated in vacuo to a dark oil, which was purified by flash chromatography over silica (25 g) eluting with cyclohexane-ether (1:1–1:4) gave the title compound (304 mg).

Mass spectrum m/z=439/441 ($MH^+$);

INTERMEDIATE 6

(2R,3R,4S,5R)-2-(6-Chloro-purin-9-yl)-5-trifluoromethoxymethyl-tetrahydro-furan-3,4-diol Acetic acid 4R-acetoxy-2R-(6-chloro-purin-9-yl)-5R-trifluoromethoxymethyl-tetrahydro-furan-3R-yl ester (345 mg) was dissolved in methanol (6 ml), cooled to 0–5° C., and tert-butylamine (0.25 ml) added. The solution was allowed to stand at 0–5° C. for 1 h, then evaporated to dryness in vacuo, to afford the title compound as a colourless foam (265 mg).

TLC $SiO_2$ ($CH_2Cl_2$-MeOH 9:1) Rf=0.31.

INTERMEDIATE 7

Acetic Acid 4R-Acetoxy-2R-(6-chloro-2-methyl-purin-9-yl)-5R-trifluoromethoxymethyl-tetrahydro-furan-3R-yl Ester 6-Chloro-2-methylpurine hydrochloride (0.734 g), 1,1,1,3,3,3-hexamethyl-disilazide (7 ml) and dry toluene (20 ml) were heated under reflux under nitrogen for 1.5 h. The mixture was evaporated in vacuo and the residue co-evaporated with toluene then dissolved in dry acetonitrile (15 ml). Acetic acid 4R-acetoxy-5R-methoxy-2R-trifluoromethoxymethyl-tetrahydro-furan-3R-yl ester (0.566 g), 1,8-diazabicycloundec-7-ene (0.48 ml) and trimethylsilyl trifluoromethanesulfonate (1.03 ml) were added, and the mixture stirred at 22° C. for 10 min then heated under reflux under nitrogen for 2 h. Further trimethylsilyl trifluoromethanesulfonate (0.7 ml) was added and the solution heated under reflux under nitrogen for a further 1.5 h. The dark mixture was added to 8% sodium bicarbonate solution (100 ml) and extracted with ethyl acetate. The organic extracts were dried (Na$_2$SO$_4$) and evaporated in vacuo and the residue purified by flash chromatography over silica (60 g) eluting with ether eluant to afford the product (290 mg)

TLC SiO$_2$ (Et$_2$O) Rf=0.17.

INTERMEDIATE 8

2-(2S-Hydroxy-(S)-cyclopentyl)-isoindole-1,3-dione (1S,2S)-2-Amino-cyclopentanol hydrochloride (1.20 g) was dissolved in a solution of sodium methoxide (497 mg) in methanol (10 ml), filtered and evaporated in vacuo. The residue was dissolved in toluene (30 ml) and phthalic anhydride (1.55 g) added, and the mixture heated under reflux for 24 h. After cooling, ethyl acetate was added and the mixture filtered. The filtrate was evaporated in vacuo and the residue purified by flash chromatography over silica (40 g) eluting with cyclohexane-ethyl acetate (2:1) to afford the title compound as a colourless solid (1.08 g).

Mass spectrum m/z 232 (MH$^+$).

INTERMEDIATE 9

2-(2S-Fluoro-(S)-cyclopentyl)-isoindole-1,3-dione 2-(2S-Hydroxy-(S)-cyclopentyl)-isoindole-1,3-dione (3.42 g) was dissolved in dry dichloromethane (55 ml) and diethylaminosulfur trifluoride (3.43 ml) added, and the solution stirred under reflux under nitrogen for 72 h. The solution was poured carefully into 8% sodium bicarbonate solution (100 ml) and the organic phase separated. The aqueous phase was further extracted with dichloromethane and the combined organic layers dried (MgSO$_4$) and evaporated in vacuo. The residue was purified by flash chromatography over silica (100 g) eluting with cyclohexane-ethyl acetate (1:1) to give the title compound as a cream powder (1.25 g).

Mass spec m/z 234 (MH$^+$), 251 (MNH$_4^+$).

INTERMEDIATE 10

(1S,2S)-2-Fluorocyclopentylamine Hydrochloride 2-(2S-Fluoro-(S)-cyclopentyl)-isoindol-1,3-dione (6.75 g), hydrazine hydrate (1.55 ml) and ethanol (200 ml) were treated with water (1.55 ml) and heated under reflux for 4 h. The mixture was cooled to 20° C. filtered and the filtrate treated with conc. hydrochloric acid to pH1. The solution was evaporated in vacuo and taken up in water, filtered, and the filtrate evaporated in vacuo. The residue was recrystallised (with hot filtration) from ethyl acetate-methanol (3:1) to afford the title compound as an off-white solid (2.59 g).

NMR δ(DMSO) 8.3 (3H, brs, —NH$_3^+$), 5.04, (1H, dm, C HF, J F-C-H, 52 Hz), 3.49 (1H, brdm, CH, J F-C-C-H 20 Hz), and 2.2–1.4 (6Hm, 3×CH$_2$).

INTERMEDIATE 11

[6R-(6-Cyclopentylamino-purin-9-yl)-2,2-dimethyl-tetrahydro-(3aR,6aR)-furo[3,4-d][1,3]dioxol-4R-yl]-methanol A solution of {2,2-dimethyl-6R-[6-chloro-purin-9-yl]-tetrahydro-(3aR,6aR)-furo[3,4-d][1,3]dioxol-4R-yl}-methanol (3 g) in cyclopentylamine (50 ml) was heated under reflux for 8 h. The solution was cooled to room temperature, concentrated in vacuo and the residue applied to a silica gel column (250 g) and eluted with ethyl acetate-:methanol (20:1) to afford the title compound as a yellow foam (3.87 g).

NMR δ(DMSO) 8.4 (1H, s, —CH), 8.26, (1H, brs, CH), 7.85 (1H, brs, NH), 6.19 (1Hd,CH), 5.4 (1Hdd, CH), 5.37 (1H brs, OH), 5.03 (1Hdd CH), 4.57 (1H brs, CH), 4.28 (1Hm, CH), 3.60 (2Hm, CH$_2$), 1.99 (2Hm, CH$_2$), 1.8–1.55 (9H, 3×CH$_2$+CH$_3$), and 1.38 (3Hs, CH$_3$).

INTERMEDIATE 12

Cyclopentyl-{9-[2,2-dimethyl-6R-(2,2,2-trifluoroethoxymethyl)-tetrahydro-(3aR,6aR)-furo[3,4-d][1,3]dioxol-4R-yl]-9H-purin-6-yl}-amine A solution of [6R-(6-cyclopentylamino-purin-9-yl)-2,2-dimethyl-tetrahydro-(3aR,6aR)-furo[3,4-d][1,3]dioxol-4R-yl]-methanol (230 mg) in tetrahydrofuran (5 ml) under nitrogen at 0° C. was treated with tri-n-butyl phosphine (0.23 ml, 186 mg) and 2,2,2-trifluoroethanol (0.07 ml, 92 mg) followed by 1,1'-azadicarbonyldipiperidine (232 mg). The mixture was stirred at 0° for 10 min then allowed to warm to 22° C. for 18 h. The mixture was then heated to 50° C. for 24 h, cooled to 22° C., and the solvent was evaporated in vacuo. The residue was purified by flash chromatography over silica (20 g). Elution with ethyl acetate afforded the title compound as a straw coloured foam (110 mg).

TLC Silica (ethyl acetate) Rf=0.45.

INTERMEDIATE 13

{2,2-Dimethyl-6R-[6-(tetrahydro-pyran-4-ylamino)-purin-9-yl]-tetrahydro-(3aR,6aR)-furo[3,4-d][1,3]dioxol-4R-yl}-methanol A solution of {2,2-dimethyl-6R-[6-chloro-purin-9-yl]-tetrahydro-(3aR,6aR)-furo[3,4-d][1,3]dioxol-4R-yl}-methanol (2.00 g), tetrahydro-pyran-4-ylamine hydrochloride (926 mg) and diisopropylethylamine (2.67 ml) in propan-2-ol (15 ml) was heated under reflux under nitrogen for 24 h and left to cool to room temperature. The amber solution was concentrated under vacuum to give a brown oil which was purified by flash chromatography over silica (115 g) with ethyl acetate:methanol (195:5) eluant. This afforded the title compound as a white foam (2.2 g).

TLC SiO$_2$ (Methanol:ethyl acetate 5:195), Rf=0.30.

INTERMEDIATE 14

{9–12,2-Dimethyl-6R-(2,2,2-trifluoro-ethoxymethyl)-tetrahydro-(3aR,6aR)-furo[3,4-d][1,3]dioxol-4R-yl[-9H-purin-6-yl}-(tetrahydro-pyran-4-yl)-amine A solution of {2,2-dimethyl-6R-[6-(tetrahydro-pyran-4-ylamino)-purin-9-yl]-tetrahydro-(3aR,6aR)-furo(3,4-d][1,3]dioxol-4R-yl}-methanol (400 mg) in tetrahydrofuran (10 ml) under nitrogen at 0° C. was treated with tri-n-butylphosphine (0.38 ml, 310 mg) and 2,2,2-trifluoroethanol (0.11 ml, 153 mg) followed by 1,1'-azadicarbonyldipiperidine (387 mg) and the mixture stirred at 0° C. for 10 min. The mixture was then stirred at 22° C. for 1 h then at 50° C. for 18 h. The mixture was cooled to 22° C. and the solvent evaporated in vacuo. The residue was purified by chromatography over silica (30 g). Elution with methanol:dichloromethane 0.35:10 gave a straw coloured oil. The oil was further purified by chromatography on alumina (20 g). Elution with ethyl acetate:cyclohexane (7:3) gave the title compound as a white foam (113 mg).

TLC SiO$_2$ (CH$_2$Cl$_2$-MeOH 200:7) Rf=0.31.

INTERMEDIATE 15

Methanesulfonic Acid 6R-(6-Chloro-purin-9-yl)-2, 2-dimethyl-tetrahydro-(3aR,6aR)-furo[3,4-d][1,3] dioxol-4R-ylmethyl Ester A solution of {2,2-dimethyl-6R-[6-chloro-purin-9-yl]-tetrahydro-(3aR,6aR)-furo[3,4-d][1,3]dioxol-4R-yl}-methanol (500 mg) in dichloromethane (20 ml) under nitrogen at 0° was treated with triethylamine (0.32 ml, 232 mg) and methanesulfonyl chloride (0.15 ml) and the mixture was stirred at 0° C. for 0.5 h. The mixture was poured into 8% sodium bicarbonate solution (20 ml) and the organic phase separated, dried (Na$_2$SO$_4$) and evaporated in vacuo to give the title compound as a white foam (577 mg).

TLC Silica ethyl acetate Rf=0.43.

INTERMEDIATE 16

Methanesulfonic Acid 6R-(6-Benzyloxy-purin-9-yl)-2,2-dimethyl-tetrahydro-(3aR,6aR)-furo[3,4-][1,3] dioxol-4R-ylmethyl Ester A solution of benzyl alcohol (1.60 ml, 1.675 g) in tetrahydrofuran (100 ml) under nitrogen at 0° C. was treated portionwise with sodium hydride (626 mg, 60% in oil) and stirred at 0° C. for 0.5 h. A solution of methanesulfonic acid 6R-(6-chloro-purin-9-yl)-2,2-dimethyl-tetrahydro-(3aR,6aR)-furo[3,4-d][1,3]dioxol-4R-ylmethyl ester (5.70 g) in tetrahydrofuran (100 ml) was added and the mixture was stirred at 0° C. for 2 h then 22° C. for 3 days. Phosphate buffer (pH6.5, 100 ml) and water (100 ml) were added and the mixture was extracted with ethyl acetate. The combined extracts were dried (Na$_2$SO$_4$) and the solvent evaporated in vacuo to give the title compound as a straw coloured viscous gum (6.67 g).

TLC SiO$_2$ (ethyl acetate:cyclohexane 7:3) Rf=0.35.

INTERMEDIATE 17

6-Benzyloxy-9-[2,2-dimethyl-6R-(2,2,2-trifluoro-ethoxymethyl)-tetrahydro-(3aR,6aR)-furo[3,4-][1,3] dioxol-4R-yl]-9H-purine 2,2,2-Trifluoroethanol (1.13 ml, 1.549 g) in DMF (dimethyl formamide) (50 ml) under nitrogen was treated with sodium hydride (563 mg, 60% in oil) and stirred for 0.5 h at 22° C. A solution of methanesulfonic acid 6R-(6-benzyloxy-purin-9-yl)-2,2-dimethyl-tetrahydro-(3aR,6aR)-furo[3,4-d][1,3]dioxol-4R-ylmethyl ester (6.67 g) in DMF (50 ml) was added and the mixture stirred at 22° C. for 18 h. Phosphate buffer (pH6.5, 100 ml) and water (300 ml) were added and the mixture was extracted with ethyl acetate. The combined extracts were washed with water, brine and dried (Na$_2$SO$_4$). Evaporation in vacuo gave a residue which was purified by flash chromatography over silica (100 g). Elution with ethyl acetate:cyclohexane (1:3 then 1:2) gave the title compound as a colourless oil (1.30 g).

TLC Silica (ethyl acetate:cyclohexane 2:3) Rf=0.27.

INTERMEDIATE 18

9-[2,2-Dimethyl-6R-(2,2,2-trifluoro-ethoxymethyl)-tetrahydro-(3aR,6aR)-furo[3,4-d][1,3]dioxol-4R-yl]-1,9-dihydro-purin-6-one A solution of 6-benzyloxy-9-[2,2-dimethyl-6R-(2,2,2-trifluoro-ethoxymethyl)-tetrahydro-(3aR,6aR)-furo[3,4-d][1,3]dioxol-4R-yl]-9H-purine (1.50 g) in ethanol (30 ml) was hydrogenated over 10% palladium on carbon (containing 50% water) (350 mg). After 35 minutes the mixture was filtered through hyflo and washed carefully with methanol. The filtrate and washings were combined and evaporated in vacuo to give the title compound as a white solid (633 mg).

Mass spectrum m/z 391 (MH$^+$).

INTERMEDIATE 19

6-Chloro-9-[2,2-dimethyl-6R-(2,2,2-trifluoro-ethoxymethyl)-tetrahydro-(3aR,6aR)-furo[3,4-d][1, 3]dioxol-4R-yl]-9H-purine Phosphorous oxychloride (0.44 ml, 726 mg) was added to a stirred solution of 9-[2,2-dimethyl-6R-(2,2,2-trifluoro-ethoxymethyl)-tetrahydro-(3aR,6aR)-furo[3,4-d][1,3] dioxol-4R-yl]-1,9-dihydro-purin-6-one (616 mg) and 4-dimethylaminopyridine (193 mg) in acetonitrile (10 ml) under nitrogen. The mixture was heated under reflux for 0.5 h. More phosphorous oxychloride (ca 0.2 ml) was added and the mixture was heated under reflux for a further 0.5 h. The mixture was cooled to 22° C. and allowed to stand for 18 h. and poured onto triethylamine (6 ml)/ice (6 ml) with cooling. The aqueous phase was acidified to pH1 with conc hydrochloric acid, then extracted with ethyl acetate. The combined organic extracts were washed with brine, dried (Na$_2$SO$_4$), and evaporated in vacuo to give a brown oil (1.3 g) which was perified by chromatography over silica (Merck 9385, 30 g). Elution with methanol:dichloromethane (2:98) gave the title compound as a beige foam (783 mg).

TLC Silica (methanol:dichloromethane 2:98) Rf=0.37.

INTERMEDIATE 20

(2R,3R,4S,5R)-2-(6-Chloro-purin-9-yl)-5-(2,2,2-trifluoroethoxymethyl)-tetrahydro-furan-3,4-diol A solution of 6-chloro-9-[2,2-dimethyl-6R-(2,2,2-trifluoro-ethoxymethyl)-tetrahydro-(3aR,6aR)-furo[3,4-d] [1,3]dioxol-4R-yl]-9H-purine (754 mg) in trifluoroacetic acid (10 ml) under nitrogen at −100° C. was treated with water (1.0 ml) and the mixture was stirred at −10° C. to 0° C. for 1.5 h. The solvent was evaporated in vacuo at 20° C., and the residue was treated with dichloromethane:ethanol:ammonia 10:8:1 (30 ml) and the solvent removed in vacuo to give an oil. This was chromatographed on silica (30 g). Eluting with methanol:dichloromethane (5:95) gave the title compound as a colourless foam (483 mg, 71%).

TLC Silica (methanol:dichloromethane 5:95) Rf=0.26.

INTERMEDIATE 21

{2,2-Dimethyl-6R-[6-(tetrahydro-pyran-4-ylamino)-purin-9-yl]-tetrahydro-(3aR,6aR)-furo[3,4-d][1,3] dioxol-4R-yl}-methanol A mixture of benzoic acid 3R,4R-bis-benzoyloxy-5R-(2, 6-dichloro-purin-9-yl)-tetrahydro-furan-2R-yl ester (8.25 g), tetrahydro-pyran-4-ylamine hydrochloride (1.92 g) and diisopropylethylamine (5.5 ml) in isopropanol (100 ml) was stirred under reflux, under nitrogen for 1.5 h. The solution was concentrated in vacuo and the residue was treated with potassium carbonate (4.5 g) in methanol (150 ml). After 24 h at 21° C. more potassium carbonate (4.5 g) was added and stirring was continued at 21° C. for 64 h. The solvent was evaporated in vacuo and the residue was absorbed on silica prior to purification by flash chromatography (250 g), with dichloromethane:methanol:ammonia (90:10:1) eluant to give an off-white foam (3.7 g). This material was dissolved in acetone (60 ml) and treated with para-toluenesulphonic acid monohydrate (2.0 g) and 2,2-dimethoxypropane (6 ml) and the resulting mixture was stirred at 22° C. overnight. The white suspension was concentrated in vacuo and the residue was partitioned between 8% aqueous sodium bicarbonate and ethyl acetate. The aqueous layer was further extracted with ethyl acetate and combined organic extracts were washed with water, brine, dried ($Na_2SO_4$) and concentrated in vacuo to a foam which was purified by flash chromatography over silica (100 g) with ethyl acetate eluant to give the title compound as a colourless foam (3.49 g).

TLC Silica (ethyl acetate) Rf=0.23.

INTERMEDIATE 22

(9-{6R-[3-(tert-Butyl-dimethyl-silanyloxy)-propoxymethyl]-2,2-dimehtyl-tetrahydro-(3aR,6aR)-furo[3,4-d][1,3]dioxol-4R-yl}-2-chloro-9H-purin-6-yl)-(tetrahydro-pyran-4-yl)-amine Sodium hydride (60% dispersion in oil, 150 mg) was added to a solution of tert-Butyl-(3-iodo-propoxy)-dimethyl-silane (720 mg) in dry dimethylformamide (5 ml) under nitrogen, and cooled in an ice-bath. After 1 h the yellow mixture was treated with {2,2-Dimethyl-6R-[6-(tetrahydro-pyran-4-ylamino)-purin-9-yl]-tetrahydro-(3aR,6aR)-furo[3,4-d][1,3]dioxol-4R-yl}-methanol (540 mg) and stirred at room temperature for 17 h. Acetic acid (0.5 ml) was added and the mixture was stirred for 1 h then poured into brine (15 ml). The aqueous mixture was extracted with ethyl acetate and the combined organic extracts were washed with water, brine, dried ($Na_2SO_4$) and concentrated in vacuo to a yellow oil. This sample was purified by flash chromatography on a silica column (5 cm diam, toluene:ethanol:triethylamine, 95:5:1 eluant), repeated on a 3 cm column, to give a pale yellow oil (269 mg).

TLC Silica (toluene:ethanol:triethylamine 90:10:1) Rf=0.39.

INTERMEDIATE 23

3-{6R-[2-Chloro-6-(tetrahydro-pyran-4-ylamino)-purin-9-yl]2,2-dimethyl-tetrahydro-(3aR,6aR)-furo[3,4-d][1,3]dioxol-4R-yl-methoxy}-propan-1-ol A solution of (9-{6R-[3-(tert-butyl-dimethyl-silanyloxy)-propoxymethyl]-2,2-dimethyl-tetrahydro-(3aR,6aR)-furo[3,4-d][1,3]dioxol-4R-yl}-2-chloro-9H-purin-6-yl)-(tetrahydro-pyran-4-yl)-amine (420 mg) in dry tetrahydrofuran (4 ml) was treated with tetra-n-butylammonium fluoride (1M in tetrahydrofuran, 12 ml) and the yellow solution was stirred at room temp for 3 h. The solvent was removed in vacuo and the residue was purified by flash chromatography over silica column (20 g, toluene:ethanol:triethylamine 90:10:1 eluant) to give the title compound as a colourless gum (299 mg).

TLC Silica (toluene:ethanol:triethylamine 90:10:1) Rf=0.28.

INTERMEDIATE 24

{2-Chloro-9-[6R-(3-fluoro-propoxymethyl)-2,2-dimethyl-tetrahydro-(3aR,6aR)-furo[3,4-d][1,3]dioxol-4R-yl]-9H-purin-6-yl}-(tetrahydro-pyran-4-yl)-amine A solution of 3-{6R-[2-Chloro-6-(tetrahydro-pyran-4-ylamino)-purin-9-yl]-2,2-dimethyl-tetrahydro-(3aR,6aR)-furo[3,4-d][1,3]dioxol-4R-ylmethoxy}-propan-1-ol (280 mg) in dichloromethane (3 ml) was treated with diethylaminosulfur trifluoride (0.13 ml) and the pale yellow solution was stirred at 22° C. for 17 h. The reaction mixture was partitioned between ethyl acetate (10 ml) and 2N sodium carbonate (10 ml), the layers were separated and the aqueous layer was re-extracted with ethyl acetate (10 ml). The combined organic extracts were washed with brine, dried ($Na_2SO_4$) and concentrated to a pale yellow oil which was purified by flash chromatography over silica (30 g) eluting with toluene:ethanol:triethylamine (95:5:1) to give the title compound as an off-white foam (173 mg).

TLC Silica (toluene:ethanol:triethylamine 90:10:1) Rf=0.41.

INTERMEDIATE 25

{9-[6R-(3-Fluoro-propoxymethyl)-2,2-dimethyl-tetrahydro-(3aR,6aR)-furo[3,4-d][1,3]dioxol-4R-yl]-9H-purin-6-yl}-(tetrahydro-pyran-4-yl)-amine A suspension of {2-chloro-9-[6R-(3-fluoro-propoxymethyl)-2,2-dimethyl-tetrahydro-(3aR,6aR)-furo[3,4-d][1,3]dioxol-4R-yl]-9H-purin-6-yl}-(tetrahydro-pyran-4-yl)-amine (120 mg), 5% palladium on carbon (50% aqueous paste, 180 mg) and ammonium formate (120 mg) in methanol (25 ml) was stirred under reflux under nitrogen for 18 h. The suspension was filtered through hyflo, evaporated in vacuo and the residue partitioned between ethyl acetate (5 ml) and water (5 ml). The aqueous layer was re-extracted with ethyl acetate (5 ml) and the combined organic extracts were washed with brine, dried ($Na_2SO_4$) and concentrated in vacuo to a semi-solid. The residue was treated with chloroform (~5 ml) and the cloudy suspension was filtered through a cotton wool plug, and the filtrate concentrated in vacuo to give the title compound as a white foam (81 mg).

TLC Silica (toluene:ethanol:triethylamine 90:10:1) Rf=0.33.

EXAMPLE 1

N-(Tetrahydro-pyran-4-yl)-5'-O-trifluoromethyladenosine

Acetic acid 4R-acetoxy-2R-(6-chloro-purin-9-yl)-5R-trifluoromethoxymethyl-tetrahydro-furan-3R-yl ester (170 mg), was heated under reflux with tetrahydro-pyran-4-ylamine hydrochloride (235 mg) and diisopropylethylamine (0.35 ml) in isopropanol (8 ml) for 20 h. After cooling, the solvent was removed in vacuo and saturated methanolic ammonia (15 ml) added and the solution allowed to stand at 22° C. for 3 h. The solvent was evaporated in vacuo and the crude product which was triturated with ether (6 ml) to afford the title compound as a colourless powder (96 mg).

Mass spectrum m/z 420 (MH$^+$); Microanalysis Found: C,45.7; H,4.9; N,16.3. $C_{16}H_{20}F_3N_5O_5$ requires C,45.8; H,4.8; N,16.7%.

EXAMPLE 2

N-(2-Pyridin-4-yl-ethyl)-5'-O-trifluoromethyladenosine (2R,3R,4S,5R)-2-(6-Chloro-purin-9-yl)-5-trifluoromethoxymethyl-tetrahydro-furan-3,4-diol (42 mg), 2-pyridin-4-yl-ethylamine (58 mg), and diisopropylethylamine (0.124 ml) were heated at 80° C. in isopropanol (5 ml) in a reactivial for 17 h. The solution was evaporated under a stream of nitrogen and purified by autoprep HPLC to afford the title compound as a colourless solid (16 mg).

Mass spectrum m/z 441 (MH+); HPLC Rt=10.39 min.

EXAMPLE 3

N-(exo-Bicyclo[2.2.1]hept-2-yl)-5'-O-trifluoromethyl-adenosine

Acetic acid 4R-acetoxy-2R-(6-chloro-purin-9-yl)-5R-trifluoromethoxymethyl-tetrahydro-furan-3R-yl ester (54 mg), (±)-exo-norbonylamine (55 mg) and di-isopropylethylamine (0.128 ml) were heated at 80° in isopropanol (7 ml) in a reactivial for 65 h. The solutions were blown down to small volume under a stream of nitrogen and saturated methanolic ammonia added and the solution allowed to stand for 3 h. The solution was evaporated in vacuo and the residue purified by chromatography using an SPE cartridge with chloroform then ethyl acetate-methanol (10:1) eluants to give the title compound as a colourless foam (51 mg).

Mass spectrum m/z=430 (MH+); LCMS Rt=4.16 min.

EXAMPLE 4

5'-O-Trifluoromethyladenosine

Acetic acid 4R-acetoxy-2R-(6-chloro-purin-9-yl)-5R-trifluoromethoxymethyl-tetrahydro-furan-3R-yl ester (53 mg) was dissolved in saturated methanolic ammonia (5 ml) and allowed to stand at 22° C. for 3 days. The sample was blown down under nitrogen and purified by flash chromatography over silica (10 g) with dichloromethane-methanol (9:1) eluant to afford the title compound as a clear gum (8.3 mg).

Mass spectrum m/z=336 (MH+); LCMS Rt=3.44 min.

EXAMPLE 5

2-[9-(3R,4S-Dihydroxy-5R-trifluoromethoxymethyl-tetrahydro-furan-2R-yl)-9H-purin-6-ylamino]-ethanesulfonic Acid Methylamide Acetic acid 4R-acetoxy-2R-(6-chloro-purin-9-yl)-5R-trifluoromethoxymethyl-tetrahydro-furan-3R-yl ester (53 mg) in isopropanol (5 ml) was treated with (2-amino-ethanesulfonic acid methylamide) (85 mg) and di-isopropylethylamine (0.211 ml) and heated in a reactivial at 80° C. for 65 h. After cooling, the solvent was removed under a stream of nitrogen, and saturated methanolic ammonia added. The solution allowed to stand at 22° C. for 3 h, then treated with 8% sodium bicarbonate solution (5 ml) and silica (5 g), and the resulting mixture evaporated to dryness in vacuo. The resulting solid mixture was applied to a column of silica (20 g) eluting with dichloromethane-methanol (20:1–5:1) to afford a colourless solid, which was recrystallised from methanol (2 ml) to afford the title compound as colourless crystals (20 mg).

Mass spectrum m/z=457 (MH+); LCMS Rt=3.62 min.

EXAMPLE 6

N-Cyclopentyl-5'-O-(2,2,2-trifluoro-ethyl)-adenosine

A solution of cyclopentyl-{9-[2,2-dimethyl-6R-(2,2,2-trifluoro-ethoxymethyl)-tetrahydro-(3aR,6aR)-furo[3,4-d][1,3]dioxol-4R-yl]-9H-purin-6-yl}-amine (100 mg) in trifluoroacetic acid (2 ml) at −10° C. under nitrogen was treated with water (0.2 ml) and the mixture stirred at −10° to 0° C. for 4 h. The solvent was evaporated in vacuo at 20° C. and the residue treated with dichloromethane:ethanol:ammonia (10:8:1) and the solvent evaporated in vacuo. The residue was purified by flash chromatography over silica (15 g). Elution with dichloromethane:ethanol:ammonia (100:8:1) gave the title compound as a colourless solid (60 mg) mp 74–6° C.

TLC Silica dichloromethane:ethanol:ammonia (100:8:1) Rf=0.29; Mass spectrum m/z–418 (MH+).

EXAMPLE 7

N-(Tetrahydro-pyran-4-yl)-5'-O-(2,2,2-trifluoro-ethyl)-adenosine

A solution of {9-[2,2-dimethyl-6R-(2,2,2-trifluoro-ethoxymethyl)-tetrahydro-(3aR,6aR)-furo[3,4-d][1,3]dioxol-4R-yl]-9H-purin-6-yl}-(tetrahydro-pyran-4-yl)-amine (90 mg) in trifluoroacetic acid (2 ml) under nitrogen at −10° C. was treated with water (0.2 ml) and the mixture stirred at −10° C. to 0° C. for 4 h. The solvent was evaporated in vacuo. The residue was purified by chromatography on silica at 20° C. and the residue treated with dichloromethane:ethanol:ammonia (10:8:1) (15 ml) and the solvent evaporated in vacuo (15 g). Elution with dichloromethane:ethanol:ammonia (75:8:1) gave the title compound as a white solid (69 mg) m.p. 80–2° C.

TLC Silica dichloromethane:ethanol:ammonia (75:8:1) Rf=0.2.

EXAMPLE 8

N-(2R-Hydroxy-cyclopent-(R)-yl)-5'-O-(2,2,2-trifluoro-ethyl)-adenosine (2R,3R,4S,5R)-2-(6-Chloro-purin-9-yl)-5-(2,2,2-trifluoroethoxymethyl)-tetrahydro-furan-3,4-diol (150 mg) in isopropanol (5 ml) under nitrogen was treated with (1R,2R)-2-amino-cyclopentanol (82 mg), and diisopropylethylamine (0.28 ml, 210 mg), and heated under reflux for 18 h. The solvent was evaporated in vacuo to give a residue which was purified by chromatography over silica (30 g). Elution with dichloromethane:ethanol:ammonia (100:10:1) gave the title compound as a beige solid (116 mg) m.p. 164–6°.

TLC Silica (dichloromethane:ethanol:ammonia 100:10:1) Rf=0.32.

EXAMPLE 9

N-(4-Fluoro-phenyl)-5'-O-(2,2,2-trifluoro-ethyl)-adenosine (2R,3R,4S,5R)-2-(6-Chloro-purin-9-yl)-5-(2,2,2-trifluoroethoxymethyl)-tetrahydro-furan-3,4-diol (125 mg) in isopropanol (5 ml) under nitrogen was treated with 4-fluoroaniline (0.08 ml, 90 mg) and diisopropylethylamine (0.28 ml, 210 mg), and the mixture was heated under reflux for 24 h. After cooling to 22° C. the mixture was filtered, the filter cake washed with isopropanol (2 ml) and ether (15 ml) and the solid dried in vacuo to give the title compound as a white solid (70 mg), m.p. 214–5°.

TLC Silica (dichloromethane:ethanol:ammonia 100:10:1) Rf=0.36

EXAMPLE 10

5'-O-(3-Fluoro-propyl)-N-(tetrahydro-pyran-4-yl)-adenosine

{9-[6R-(3-Fluoro-propoxymethyl)-2,2-dimethyl-tetrahydro-(3aR,6aR)-furo[3,4-d][1,3]dioxol-4R-yl]-9H- purin-6-yl}-(tetrahydro-pyran-4-yl)-amine (79 mg) was dissolved in ice-cold trifluoroacetic acid (0.8 ml), treated with water (0.08 ml) then stirred at 0–5° C. for 1 h. The excess trifluoroacetic acid was removed under vacuum at 30° C., and the residue was purified by flash chromatography on a silica column (10 g) with dichloromethane:methanol:ammonia (94:6:1) eluant to give the title compound as a colourless foam (52 mg).

Mass spectrum m/z 412 (MH$^+$); TLC Silica (dichloromethane:methanol:ammonia 94:6:1) Rf=0.14.

EXAMPLE 11

2-Chloro-5'-O-(3-fluoro-propyl)-N-(tetrahydro-pyran-4-yl)-adenosine

A solution of {2-chloro-9-[6R-(3-fluoro-propoxymethyl)-2,2-dimethyl-tetrahydro-(3aR,6aR)-furo[3,4-d][1,3]dioxol-4R-yl]-9H-purin-6-yl}-(tetrahydro-pyran-4-yl) amine (50 mg) in trifluoroacetic acid (0.5 ml) at 0° C. was treated with water (0.05 ml) and the reaction mixture was stirred at 0° C. for 30 min. Excess trifluoroacetic acid was removed in vacuo at 30° C. and the residue was purified by flash chromatography over silica (10 g) with dichloromethane:methanol:ammonia (94:6:1) eluant to give the title compound as a colourless foam (32 mg).

TLC Silica (dichloromethane:methanol:ammonia 94:6:1) Rf=0.18; Mass spectrum m/z=446 (MH$^+$).

By analagous methods the following Examples were prepared:

EXAMPLE 12

N-(2S-Fluoro-cyclopent-(S)-yl)-5'-O-trifluoromethyl-adenosine
Prepared from Intermediate 6
Mass spectrum m/z 422 (MH$^+$); HPLC R$_t$=19.24 min.

EXAMPLE 13

N-(Tetrahydro-thiopyran-4-yl)-5'-O-trifluoromethyl-adenosine
Prepared from Intermediate 6
Mass spectrum m/z 436 (MH$^+$); HPLC R$_t$=17.61 min.

EXAMPLE 14

N-(3,4-Difluoro-phenyl)-5'-O-trifluoromethyl-adenosine
Prepared from Intermediate 6
Mass spectrum m/z 448 (MH$^+$); HPLC R$_t$=25.44 min.

EXAMPLE 15

N-(3-Fluoro-phenyl)-5'-O-trifluoromethyl-adenosine
Prepared from Intermediate 6
Mass spectrum m/z 430 (MH$^+$); HPLC R$_t$=24.65 min.

EXAMPLE 16

N-(1,1-Dioxo-hexahydro-1.delta.6-thiopyran-4-yl)-5'-O-trifluoromethyl-adenosine
Prepared from Intermediate 5
LC/MS; R$_t$=3.62 min; Mass spectrum m/z 468 (MH$^+$).

EXAMPLE 17

N-tert-Butyl-5'-O-trifluoromethyl-adenosine
Prepared from Intermediate 5
LC/MS; R$_t$=4.12 min; Mass spectrum m/z 392 (MH$^+$).

EXAMPLE 18

4-[9-(3R,4S-Dihydroxy-5R-trifluoromethoxymethyl-tetrahydro-furan-2R-yl)-9H-purin-6-ylamino]-piperidine-1-carboxylic Acid Ethyl Ester
Prepared from Intermediate 5
Mass spectrum m/z 491 (MH$^+$); Nmr δ (CDCl$_3$) 8.25 (1Hs, CH[heterocyclic]), 8.15(1Hs,CH[heterocyclic]), 6.05 (1Hd, CH), 4.7 (1Hm, CH), 4.0–4.5 (9Hm, 5×CH+2×CH$_2$), 3.1 (2H brt, CH$_2$), 2.08 (2H brd, 2×CH), 1.55 (2H brq, 2×CH), and 1.28 (3Ht, CH$_3$).

EXAMPLE 19

N-(2S-Hydroxy-cyclopent-(S)-yl)-5'-O-trifluoromethyl-adenosine
Prepared from Intermediate 5
LC/MS; R$_t$=3.71 min; Mass spectrum m/z 420 (MH$^+$).

EXAMPLE 20

N-(rel-2,3-Dihydroxy-propyl)-5'-O-trifiuoromethyl-adenosine
Prepared from Intermediate 5
LC/MS; R$_t$=3.43 min; Mass spectrum m/z 410 (MH$^+$).

EXAMPLE 21

N-(Tetrahydro-furan-3R-yl)-5'-O-trifluoromethyl-adenosine
Prepared from Intermediate 5
LC/MS; R$_t$=3.62 min; Mass spectrum m/z 406 (MH$^+$).

EXAMPLE 22

N-(Tetrahydro-furan-3S-yl)-5'-O-trifluoromethyl-adenosine
Prepared from Intermediate 5
LC/MS; R$_t$=3.62 min; Mass spectrum m/z 406 (MH$^+$).

EXAMPLE 23

N-{2-[9-(3R,4S-Dihydroxy-5R-trifluoromethoxymethyl-tetrahydro-furan-2R-yl)-9H-purin-6-ylamino]-ethyl}-acetamide
Prepared from Intermediate 5
LC/MS; R$_t$=3.53 min; Mass spectrum m/z 421 (MH$^+$).

EXAMPLE 24

4-[9-(3R,4S-Dihydroxy-5R-trifluoromethoxymethyl-tetrahydro-furan-2R-yl)-2-methyl-9H-purin-6-ylamino]-piperidine-1-carboxylic Acid Ethyl Ester
Prepared from Intermediate 5
LC/MS; R$_t$=3.97 min; Mass spectrum m/z 505 (MH$^+$).

EXAMPLE 25

2-Methyl N-(tetrahydro-pyran-4-yl)-5'-O-trifluoromethyl-adenosine
LC/MS; R$_t$=3.72 min; Mass spectrum m/z 434 (MH$^+$).

EXAMPLE 26

N-(2-Chloro-4-fluoro-phenyl)-5'-O-trifluoromethyl-adenosine
Acetic acid 4R-acetoxy-2R-(6-chloropurin-9-yl)-5R-trifluoromethoxymethyl-tetrahydro-furan-3R-yl ester (0.16 g), 2-chloro-4-fluoroaniline (0.26 ml), palladium acetate (8 mg), R-BINAP (R-(+)-2,2'-Bis(diphenylphosphino)-1,1'-binaphthyl) (33 mg) and cesium carbonate (0.16 g) in 1.2 ml of toluene were heated in a reactivial at 85–91° C. for 16 h. The reaction mixture was cooled to room temperature and quenched with water (20 ml) and extracted with dichloromethane (3×50 ml). The organic extracts were dried (MgSO$_4$) and evaporated in vacuo. The resulting residue was purified by flash chromatography over silica (8 g Biotage column) eluting with cyclohexane-ethyl acetate 9:1–6:4) to give a clear oil which was dissolved in 1 ml of methanol, cooled to 0–5° C. and treated with t-butylamine (0.05 ml). The mixture was kept at this temperature for 1 h and evaporated to dryness in vacuo to give the title compound (67 mg) as a white solid.

LC/MS; R$_t$=3.04 min; Mass spectrum m/z 464 (MH$^+$), 466 (MH$^+$+2).

EXAMPLE 27

N-(4-Chloro-2-fluoro-phenyl)-5'-O-trifluoromethyl-adenosine

Prepared from Intermediate 5 by analogous method to Example 26.

LC/MS; R$_t$=3.16 min; Mass spectrum m/z 464 (MH$^+$), 466 (MH$^+$+2).

Reporter Gene Experiments

Agonist activity was measured in Chinese hamster ovary (CHO) cells containing the CRE/SPAP/HYG (CRE=cyclic AMP response element; HYG=hygromycin resistance; SPAP=secreted placental alkaline phosphatase) reporter gene elements, which upon stimulation of cAMP levels produced SPAP. A cell line was used, which was stably transfected with either the human adenosine A1 receptor or the human adenosine A3 receptor in addition to the above elements. Cells were plated out in 96-well plates in culture medium and incubated at 37° C. for 1 hour. For measurement of potency, agonists were added to the appropriate wells at a concentration range of approximately $10^{-10}$–$10^{-5}$M. 15 Min later, cAMP levels were stimulated by addition of a maximal concentration of forskolin. All cells were then incubated for a further 5 hours at 37° C., and cooled to room temperature, after which a substrate for the phosphatase (para-nitrophenol phosphate, pNPP), which is converted by SPAP to a coloured reagent) was then added and the 96-well plates were read in a plate reader. From these readings, the concentration-dependence of the inhibition by the agonist for forskolin-stimulated SPAP production can be calculated. One of the agonists tested on each 96-well plate was the standard non-selective agonist, N-ethylcarboxamidoadenosine (NECA), and the potency of all test agonists is expressed relative to that of the NECA standard.

(ECR=equipotent concentration ratio relative to NECA=1)

Result

TABLE 1

Biological Data. A1, A3 Receptor, Receptor Gene Assay ECR

| Example | A1 | A3 |
|---------|------|-------|
| 1 | 8.40 | >129 |
| 2 | 185.5 | — |
| 3 | 5.60 | 143.5 |

TABLE 1-continued

Biological Data. A1, A3 Receptor, Receptor Gene Assay ECR

| Example | A1 | A3 |
|---------|--------|-------|
| 4 | 80.7 | 81.6 |
| 5 | 33.2 | >212 |
| 6 | 8.70 | 7.7 |
| 7 | — | — |
| 8 | 239.40 | — |
| 9 | 298 | 19.7 |
| 10 | — | — |
| 11 | — | — |
| 12 | 1.87 | >226 |
| 13 | 11.1 | >276 |
| 14 | 20.50 | 197.3 |
| 15 | 23.2 | — |
| 16 | 79.50 | >207 |
| 17 | 138.8 | >207 |
| 18 | 5.32 | >202 |
| 19 | 12.10 | >150 |
| 20 | 24.10 | 284.5 |
| 21 | 10.90 | >175 |
| 22 | 10.40 | >63 |
| 23 | 12.52 | >175 |
| 24 | 51.70 | >134 |
| 25 | 32 | — |

What is claimed is:
1. A compound of formula (I):

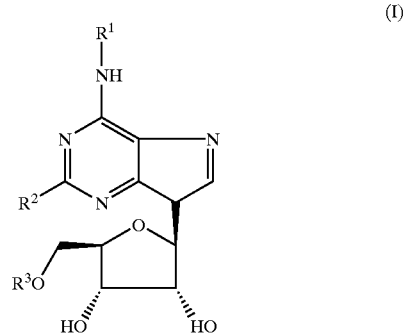

wherein R$^2$ represents C$_{1-3}$ alkyl, halogen or hydrogen;
R$^3$ represents a fluorinated straight or branched alkyl group of 1–6 carbon atoms;
R$^1$ represents a group selected from the group consisting of:
(1) —(alk)$_n$—(C$_{3-7}$)cycloalkyl group or —(alk)$_n$—(C$_{4-7}$)bridged cycloalkyl group, wherein either said group is optionally substituted by one or more substituents selected from the group consisting of OH, halogen, and —(C$_{1-3}$) alkoxy; wherein (alk) represents C$_{1-3}$ alkylene and n represents 0 or 1;
(2) an aliphatic heterocyclic group of 4 to 6 membered rings containing at least one heteroatom selected from the group consisting of O, N and S optionally substituted by one or more substituents selected from the group consisting of —(C$_{1-3}$)alkyl, —CO$_2$—(C$_{1-4}$) alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) and =O; where there is a sulfur atom in the heterocyclic ring, said sulfur is optionally substituted by (=O)$_n$, where n is 1 or 2;
(3) straight or branched C$_{1-12}$ alkyl, optionally including one or more O, S(=O)$_n$ (where n is 0, 1 or 2), or N groups substituted within the alkyl chain, wherein said alkyl is optionally substituted by one or more of the following groups: phenyl, halogen, hydroxy or $NR^aR^b$ wherein $R^a$ and $R^b$ both represent $C_{1-3}$alkyl or hydrogen;

(4) a fused bicyclic aromatic ring:

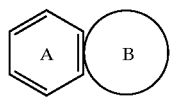

wherein B represents a 5 or 6 membered heterocyclic aromatic group containing 1 or more O, N or S atoms wherein the bicyclic ring is attached to the nitrogen atom of formula (I) via a ring atom of ring A and ring B is optionally substituted with —$CO_2$—($C_{1-3}$alkyl);

(5) a phenyl group optionally substituted by one or more substituents selected from the group consisting of:
—halogen, —$SO_3H$, —(alk)$_n$OH, —(alk)$_n$-cyano, —(O)$_n$—($C_{1-6}$)-alkyl (optionally substituted by one or more halogens), —(alk)$_n$-nitro, —(O)$_m$, —(alk)$_n$, —$CO_2R^c$, —(alk$_n$)—$CONR^cR^d$, —(alk)$_n$$OR^c$, —(alk)$_n$—$COR^c$, —(alk)$_n$—$SOR^e$, —(alk)$_n$, —$SO_2NR^cR^d$, —(alk)$_n$, —$SO_2NR^cR^d$, —(alk)$_n$$OR^c$, —(alk)$_n$—(CO)$_m$—$NHSO_2R^e$, —(alk)$_n$—$NHCOR^e$, and —(alk)$_n$—$NR^cR^d$ wherein m and n are 0 or 1 and alk represents a $C_{1-6}$ alkylene group or $C_{2-6}$ alkenylenyl group; and (6) a phenyl group substituted by a 5 or 6 membered heterocyclic aromatic group, said heterocyclic aromatic group optionally being substituted by $C_{1-3}$ alkyl or $NR^cR^d$;

$R^c$ and $R^d$ may each independently represent hydrogen, or $C_{1-3}$ alkyl or when part of a group $NR^cR^d$, $R^c$ and $R^d$ together with the nitrogen atom may form a 5 or 6 membered heterocyclic ring optionally containing other heteroatoms which heterocyclic ring may optionally be substituted further by one or more $C_{1-3}$ alkyl groups;

$R^e$ represents $C_{1-3}$ alkyl;
and physiologically acceptable solvates or salts thereof.

2. The compound according to claim 1 wherein $R^3$ represents a $C_{1-3}$ fluoroalkyl group.

3. The compound according to claim 2 wherein $R^3$ represents a fluoromethyl group.

4. The compound according to claim 1 wherein $R^3$ represents trifluoromethyl group.

5. The compound according to claim 1 wherein $R^2$ represents hydrogen, methyl or halogen.

6. The compound according to claim 5 wherein $R^2$ represents hydrogen, methyl or chloro.

7. The compound according to claim 1 wherein $R^1$ represents (alk)$_n$—$C_{3-6}$-cycloalkyl wherein n is 0 or 1 and the said cycloalkyl is either substituted by a halogen or OH or is unsubstituted.

8. The compound according to claim 7 wherein n represents zero.

9. The compound according to claim 8 wherein the cycloalkyl is monosubstituted by OH or fluro.

10. The compound according to claim 7 wherein the cycloalkyl ring has 5 carbon members.

11. The compound according to claim 1 wherein $R^1$ represents a substituted or unsubstituted aliphatic heterocyclic group, the substituent being selected from the group consisting of —($CO_2$)—($C_{1-4}$)alkyl, —CO—($C_{1-3}$)alkyl, —S(=O)$_n$—($C_{1-3}$)alkyl, and by $CONR^aR^b$, and when there is a heteroatom S in the ring, this heteroatom may optionally be substituted by (=O)$_n$ where n is 0, 1 or 2.

12. The compound according to claim 11 wherein the heterocyclic ring is unsubstituted or the substituents are —$CO_2$($C_{1-4}$)alkyl, or when the heteroatom is S, the substituent (=O)$_n$ is attached to the heterocyclic S atom.

13. The compound according to claim 12 where in the sulfur heteroatom is unsubstituted.

14. The compound according to claim 11 wherein the aliphatic heterocyclic group is either unsubstituted, or when substituted the substituent is —CO2($C_{1-4}$)alkyl, the heteroatom is N, and the substituent is attached directly to the ring N atom.

15. The compound according to claim 11 wherein the heterocyclic ring is 5 or 6 membered.

16. The compound according to claim 1 wherein $R^1$ represents a straight or branched alkyl of 1–5 carbon atoms optionally with at least one S(=O)$_n$ where n is 0, 1 and/or NH substituted in the chain.

17. The compound according to claim 16 wherein when there is S(=O)$_n$ in the chain n is 1 or 2.

18. The compound according to claim 15 wherein the alkyl group may be unsubstituted or substituted by at least one OH group.

19. The compound according to claim 1 wherein $R^1$ represents a phenyl group substituted by one or more substituents selected from OH and halogen.

20. The compound according to claim 19 wherein the phenyl group is substituted in the 2 and 4 positions.

21. The compound according to claim 20 where in both substituents are halogen.

22. The compound according to claim 21 wherein the 2-substituent is fluoro and the 4-substituent is chloro.

23. A compound according to claim 1 which is:

$N^6$-(tetrahydro-pyran-4-yl)-5'-O-trifluoromethyl-adenosine;

$N^6$-(2-pyridin-4-yl-ethyl)-5'-O-trifluoromethyl-adenosine;

$N^6$-(2S-fluoro-cyclopent-(S)-yl)-5'-O-trifluoromethyl-adenosine;

$N^6$-(tetrahydro-thiopyran-4-yl)-5'-O-trifluoromethyl-adenosine;

$N^6$-(3,4-difluoro-phenyl)-5'-O-trifluoromethyl-adenosine;

$N^6$-(3-fluoro-phenyl)5'-O-trifluoromethyl-adenosine;

$N^6$-(exo-bicyclo[2.2.1]hept-2-yl)-5'-O-trifluoromethyl-adenosine;

$N^6$-(1,1-dioxo-hexahydro-1.delta.6-thiopyran-4-yl)-5'-O-trifluoromethyl adenosine;

$N^6$-tert-butyl-5'-O-trifluoromethyl-adenosine;

4-[9-(3R,4S-dihydroxy-5R-trifluoromethoxymethyl-tetrahydro-furan-2R-yl) 9H-peurin-6-ylamino]N-ethoxycarbonylpiperidine;

$N^6$-(2S-hydroxy-cyclopent-(S)-yl)-5'-O-trifluoromethyl-adenosine;

$N^6$-(rel-2,3-dihydroxy-propyl)-5'-O-trifluoromethyl-adenosine;

$N^6$-(tetrahydro-furan-3R-yl)-5'-O-trifluoromethyl-adenosine;

$N^6$-(tetrahydro-furan-3S-yl)-5'-O-trifluoromethyl-adenosine;

$N^6$-[2-(acetylamino)ethyl]-5'-O-(trifluoromethyl) adenosine;

5'-O-trifluoromethyl-adenosine;

2-[9-(3R,4S-dihydroxy-5R-trifluoromethoxymethyl-tetrahydro-furan-2R-yl) 9H-purin-6-ylamino]-ethanesulfonic acid methylamide;

4-[9-(3R,4S-dihydroxy-5R-trifluoromethoxymethyl-tetrahydro-furan-2R-yl) 2-methyl-9H-purin-6-ylamino]N-ethoxycarbonylpiperidine;

2-methyl N-(tetrahydro-pyran-4-yl)-5'-O-trifluoromethyl-adenosine;

5'-O-(3-fluoro-propyl)-N-(tetrahydro-pyran-4-yl)-adenosine;

2-chloro-5'-O-(3-fluoro-propyl)-N-(tetrahydro-pyran-4-yl)-adenosine;

$N^6$-cyclopentyl-5'-O-(2,2,2-trifluoro-ethyl)-adenosine;

$N^6$-(tetrahydro-pyran-4-yl)-5'-O-(2,2,2-trifluoro-ethyl)-adenosine;

$N^6$-(2R-hydroxy-cyclopent-(1R)-yl)-5'-O-(2,2,2-trifluoro-ethyl)-adenosine; or $N^6$-(4-fluoro-phenyl)-5'-O-(2,2,2-trifluoro-ethyl)-adenosine.

24. A pharmaceutical composition comprising a compound according to claim 7 together with a pharmaceutically acceptable carrier and/or excipient.

25. A method for preparing a compound according to claim 1 which method comprises reaction of a compound of formula (II):

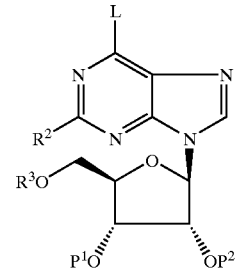

(II)

wherein L represents a leaving group, $P^1$ and $P^2$ represent hydrogen or a suitable protecting group, and $R^1$, $R^2$ and $R^3$ are as defined in claim 1 with a compound $R^1$—$NH_2$ or salt thereof under basic conditions.

26. A method of treating a patient suffering from or susceptible to ischemic heart disease, peripheral vascular disease or stroke, or suffering pain, convulsions or epilepsy comprising administering to the patient a therapeutically effective amount of a compound according to claim 1.

* * * * *